United States Patent [19]

Bajwa, deceased et al.

[11] Patent Number: 4,599,409

[45] Date of Patent: Jul. 8, 1986

[54] BISAMIDINE DERIVATIVES OF 5,10-DIOXO-4,5,9,10-TETRAHYDRO-4,9-DIOXOPYRENES, OF 6(5H)-PHENANTHRIDONES, AND OF PHENANTHRIDINES, USEFUL AS CHEMOTHERAPEUTIC AGENTS

[75] Inventors: Balbir S. Bajwa, deceased, late of Bombay, by Sarabjeet Bajwa, Surjeet K. Bajwa, heirs; Dipak K. Chatterjee, Bombay; Bimal N. Ganguli, Bombay; Jürgen Reden, Bombay; Noel J. de Souza, Bombay, all of India

[73] Assignee: Hoechst Aktiengesellschaft, Fed. Rep. of Germany

[21] Appl. No.: 580,181

[22] Filed: Feb. 15, 1984

[30] Foreign Application Priority Data

Feb. 17, 1983 [DE] Fed. Rep. of Germany ....... 3305329

[51] Int. Cl.$^4$ ................ C07D 413/00; C07D 403/00; C07D 493/06
[52] U.S. Cl. .................... 544/126; 544/296; 544/333; 544/361; 546/109; 546/110; 546/187; 546/203; 546/204; 548/518; 549/277; 549/278
[58] Field of Search ............... 549/277, 278; 424/256, 424/279, 248, 250; 544/126, 361, 333; 546/107, 108, 109, 110; 514/298, 255, 253, 256, 237, 227

[56] References Cited

U.S. PATENT DOCUMENTS

| | | | |
|---|---|---|---|
| 2,303,517 | 12/1942 | Walls et al. | 546/109 |
| 2,495,051 | 1/1950 | Barbar | 546/109 |
| 3,122,553 | 2/1964 | Seneca | 546/107 |
| 3,838,131 | 9/1974 | Gauthier | 546/108 |
| 3,953,455 | 4/1976 | Meyer et al. | 546/108 |

FOREIGN PATENT DOCUMENTS

| | | | |
|---|---|---|---|
| 1083826 | 6/1960 | Fed. Rep. of Germany . | |
| 1645907 | 7/1970 | Fed. Rep. of Germany . | |
| 1802639 | 5/1969 | Netherlands | 546/108 |
| 816236 | 7/1959 | United Kingdom | 546/108 |
| 594113 | 2/1978 | U.S.S.R. | 546/108 |
| 887567 | 12/1981 | U.S.S.R. | 546/108 |

OTHER PUBLICATIONS

Chemical Abstracts, vol. 91, No. 17, (1979), 140744z.

*Primary Examiner*—Donald G. Daus
*Assistant Examiner*—Cecilia Shen
*Attorney, Agent, or Firm*—Finnegan, Henderson, Farabow, Garrett & Dunner

[57] ABSTRACT

The present invention relates to new bisamidine derivatives of polycyclic compounds such as 5,10-dioxo-4,5,9,10-tetrahydro-4,9-dioxapyrene-6(5H)-phenanthridone and 5,10-dioxo-4,5,9,10-tetrahydro-4,9-dioxapyrenephenanthridine and to a process for their preparation. The polycyclic bisamidines according to the invention are distinguished by valuable chemotherapeutic properties, such as, for example, an action against amoebas and trichomonads.

6 Claims, No Drawings

BISAMIDINE DERIVATIVES OF 5,10-DIOXO-4,5,9,10-TETRAHYDRO-4,9-DIOXOPYRENES, OF 6(5H)-PHENANTHRIDONES, AND OF PHENANTHRIDINES, USEFUL AS CHEMOTHERAPEUTIC AGENTS

The present invention relates to new bisamidine derivatives of polycyclic molecules of the formula I

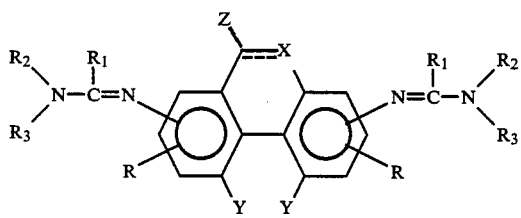

in which
- R denotes hydrogen, $C_1$–$C_3$-alkyl, $C_1$–$C_3$-alkoxy, halogen, nitro or amino,
- $R_1$ denotes hydrogen, a $C_1$–$C_6$-alkyl group which is unsubstituted or substituted by the amino or di-$C_1$–$C_3$-alkylamino group, or a di-$C_1$–$C_3$-alkylamino group,
- $R_2$ and $R_3$ individually denote a $C_1$–$C_6$-alkyl group or, together with the nitrogen atom to which they are attached, denote a heterocyclic group, or
- $R_1$ and $R_2$, together with the carbon atom and the nitrogen atom to which they are attached, denote a heterocyclic group,
- X and Z each denote oxygen or
- X represents the —NH— group and Z represents oxygen or
- X represents nitrogen and Z represents hydrogen, halogen, $C_1$–$C_6$-alkoxy, amino, mono-$C_1$–$C_6$-alkylamino di-$C_1$–$C_6$-alkylamino or a heterocyclic group, and
- Y represents hydrogen or, if X and Z each denote oxygen, represents the bridge

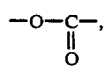

which forms an additional ring system,
and to pharmaceutically acceptable salts thereof.

5,10-Dioxo-4,5,9,10-tetrahydro-4,9-dioxapyrene, a tetracyclic molecule of the formula I in which X and Z denote oxygen, may be mentioned as an example of polycyclic molecules according to the invention.

The present invention therefore relates to bisamidine derivatives of the following formula Ia

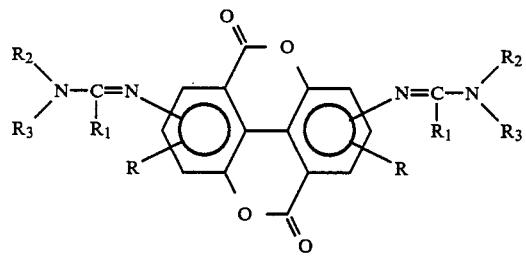

The tricyclic 6(5H)-phenanthridone of the formula I in which the ring system formed by the

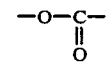

bridge is lacking, and in which X denotes the NH group and Z denotes oxygen, could also be mentioned as an example of polycyclic molecules according to the invention. Consequently, bisamidine derivatives of the following formula Ib constitute a further subject of the invention:

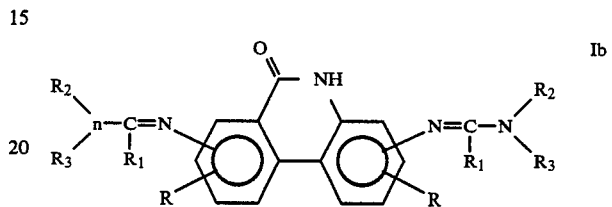

The tricyclic phenanthridine of the formula I in which the

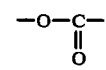

bridge constituting the additional ring bond is also lacking, X denotes nitrogen and Z denotes hydrogen, halogen, $C_1$–$C_6$-alkoxy, amino, mono-$C_1$–$C_6$-alkylamino or di-$C_1$–$C_6$-alkylamino, of the following formula Ic

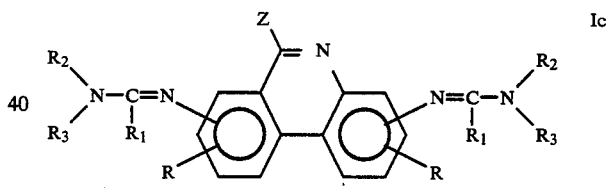

could be mentioned as a third example of polycyclic molecules according to the invention. In the formulae Ia, Ib and Ic R denotes hydrogen. If $R_1$, $R_2$ and $R_3$ represent alkyl groups, alkyl groups having up to 3 carbon atoms, such as, for example, methyl, ethyl, n-propyl or isopropyl, are preferentially suitable.

Dialkylamino groups represented by $R_1$ are preferably dimethylamino or diethylamino.

If Z represents alkoxy, alkylamino or dialkylamino groups, groups of this type having 1–3 carbon atoms are preferentially suitable.

Nitrogen-containing heterocyclic groups are preferably pyrrolidine, piperidine, imidazoline or pyrimidine which are optionally substituted by one or more $C_1$–$C_3$-alkyl groups.

Examples which can be mentioned of pharmaceutically acceptable salts, according to the invention, of the bisamidine derivatives are inorganic acid addition salts, such as hydrochlorides, hydriodides, hydrofluorides, sulfates or phosphates, or organic acid addition salts, such as acetates, oxalates, tartrates, citrates, maleates, fumarates or methanesulfonates, which acid addition salts are obtained by reaction with the corresponding acids in the customary manner.

Preferred bisamidine derivatives, according to the invention, of the 5,10-dioxo-4,5,9,10-tetrahydro-4,9-dioxapyrene of the formula Ia are those in which R denotes hydrogen and the amidino derivatives are in the 2-position or 7-position, $R_1$ represents a $C_1$-$C_6$-alkylamino or di-$C_1$-$C_6$-alkylamino group, $R_2$ and $R_3$ each individually denote a $C_1$-$C_6$-alkyl group or, together with the nitrogen atom to which they are attached, form a heterocyclic structure, and $R_1$ and $R_2$, together with the carbon atom and the nitrogen atom to which they are attached, denote a heterocyclic group, and pharmaceutically acceptable salts thereof.

The following are particularly preferred bisamidine derivatives, according to the invention, of the 5,10-dioxo-4,5,9,10-tetrahydro-4,9-dioxapyrene of the formula Ia:
1. 2,7-Di-(N',N'-diethylaminomethyleneamino)-5,10-dioxo-4,5,9,10-tetrahydro-4,9-dioxapyrene dihydrochloride.
2. 2,7-Di-(N',N'-diethylaminoethylideneamino)-5,10-dioxo-4,5,9,10-tetrahydro-4,9-dioxapyrene.
3. 2,7-Di-(N',N'-diethylaminoethylideneamino)-5,10-dioxo-4,5,9,10-tetrahydro-4,9-dioxapyrene dihydrochloride.
4. 2,7-Di-(N-methylpyrrolidin-2-ylideneamino)-5,10-dioxo-4,5,9,10-tetrahydro-4,9-dioxapyrene dihydrochloride.
5. 2,7-Di-(N-methylpiperid-2-ylideneamino)-5,10-dioxo-4,5,9,10-tetrahydro-4,9-dioxapyrene dihydrochloride.
6. 2,7-Di-(piperidinomethyleneamino)-5,10-dioxo-4,5,9,10-tetrahydro-4,9-dioxapyrene dihydrochloride monohydrate.

Some new bisamidine derivatives of the 5,10-dioxo-4,5,9,10-tetrahydro-4,9-dioxapyrene of the formula Ia are listed in the following table:

| $R_1$ | $R_2$ | $R_3$ | Salt | Mp. (°) |
|---|---|---|---|---|
| H | $CH_3$ | $CH_3$ | — | 300 |
| H | $CH_3$ | $CH_3$ | 2HCl | 300 |
| H | $C_2H_5$ | $C_2H_5$ | — | 232–5 |
| H | $C_2H_5$ | $C_2H_5$ | 2HCl | 282 (Decomp.) |
| $CH_3$ | $CH_3$ | $CH_3$ | — | 276–8 |
| $CH_3$ | $CH_3$ | $CH_3$ | 2HCl | 298–91 (Decomp.) |
| $CH_3$ | $C_2H_5$ | $C_2H_5$ | — | 220–2 |
| $CH_3$ | $C_2H_5$ | $C_2H_5$ | 2HCl | 284–6 (Decomp.) |
| $CH_3$ | $C_2H_5$ | $C_2H_5$ | $2CH_3SO_3H$ | 286–88 (Decomp.) |
| $CH_3$ | $C_2H_5$ | $C_2H_5$ | $2CH_2COOHCHOHCH_2COOH$ | 198–99 |
| $CH_3$ | $C_2H_5$ | $C_2H_5$ | 2HI | 310 (Decomp.) |
| $CH_3$ | $C_2H_5$ | $C_2H_5$ | $2H_2SO_4$ | 294–96 (Decomp.) |
| $CH_3$ | $C_3H_7$ | $C_3H_7$ | — | 201–3 |
| $CH_3$ | $C_3H_7$ | $C_3H_7$ | 2HCl | 266–70 (Decomp.) |
| $C_2H_5$ | $CH_3$ | $CH_3$ | — | 246–8 |
| $C_2H_5$ | $CH_3$ | $CH_3$ | 2HCl | 265–7 (Decomp.) |
| H | —$(CH_2)_4$— | | — | 265–7 (Decomp.) |
| H | —$(CH_2)_4$— | | $2HCl.H_2O$ | 283–5 (Decomp.) |
| H | —$(CH_2)_5$— | | — | 275 (Decomp.) |
| H | —$(CH_2)_5$— | | $2HCl.H_2O$ | 290–93 (Decomp.) |
| —$(CH_2)_3$— | | $CH_3$ | — | 274–75 |
| —$(CH_2)_3$— | | $CH_3$ | 2HCl | 300 (Decomp.) |
| —$(CH_2)_3$— | | $C_2H_5$ | — | 310–11 (Decomp.) |
| —$(CH_2)_3$— | | $C_2H_5$ | 2HCl | 300 |
| —$(CH_2)_3$— | | $CH_3$ | — | 260–62 |
| —$(CH_2)_4$— | | $CH_3$ | 2HCl | 277–79 |
| $N(CH_3)_2/CH_3$ | $CH_3$ | | — | 248–52 |

Preferred bisamidine derivatives of the 6(5H)-phenanthridone of the formula Ib are those in which R represents hydrogen, the amidino group is in the 3-position and 8-position, $R_1$ represents hydrogen or a $C_1$-$C_6$-alkyl group, and $R_2$ and $R_3$ each individually represent a $C_1$-$C_6$-alkyl group or, together with the nitrogen atom to which they are attached, form a heterocyclic structure, or in which $R_1$ and $R_2$, together with the carbon atom and the nitrogen atom to which they are attached, form a heterocyclic structure, and also pharmaceutically acceptable salts thereof.

The following are particularly preferred bisamidine derivatives, according to the invention, of the 6-(5H)-phenanthridone of the formula Ib:
1. 3,8-Di-(N',N'-dimethylaminoethylideneamino)-6(5H)-phenanthridone dihydrochloride dihydrate.
2. 3,8-Di-(N',N'-diethylaminomethyleneamino)-6(5H)-phenanthridone.
3. 3,8-Di-(N',N'-diethylaminomethyleneamino)-6(5H)-phenanthridone dihydrochloride dihydrate.
4. 3,8-Di-(N'-methylpyrrolidin-2-ylideneamino)-6(5H)-phenanthridone dihydrochloride dihydrate.
5. 3,8-Di-(piperidinomethyleneamino)-6(5H)-phenanthridone dihydrochloride.
6. 3,8-Di-(pyrroldinomethyleneamino)-6(5H)-phenanthridone.

Some new bisamidine derivatives of the 6(5H)-phenanthridone of the formula Ib are listed in the following table:

| $R_1$ | $R_2$ | $R_3$ | Salt | Mp. (°) | |
|---|---|---|---|---|---|
| H | $C_2H_5$ | $C_2H_5$ | — | 240–1 | (Decomp.) |
| H | $C_2H_5$ | $C_2H_5$ | $2HCl.2H_2O$ | 281–3 | (Decomp.) |
| $CH_3$ | $CH_3$ | $CH_3$ | — | 257–9 | (Decomp.) |
| $CH_3$ | $CH_3$ | $CH_3$ | $2HCl.2H_2O$ | 268–70 | (Decomp.) |
| $CH_3$ | $C_2H_5$ | $C_2H_5$ | — | 220–2 | |
| $CH_3$ | $C_2H_5$ | $C_2H_5$ | 2HCl | 255–7 | (Decomp.) |
| $C_2H_5$ | $CH_3$ | $CH_3$ | — | 272–4 | |
| $C_2H_5$ | $CH_3$ | $CH_3$ | $2HCl.2H_2O$ | 223–5 | |
| H | —$(CH_2)_4$— | | — | 280 | (Decomp.) |
| H | —$(CH_2)_4$— | | 2HCl | 300 | (Decomp.) |
| H | —$(CH_2)_5$— | | — | 152–3 | |
| H | —$(CH_2)_5$— | | 2HCl | 255–7 | (Decomp.) |
| —$(CH_2)_3$— | | $CH_3$ | — | 259–61 | (Decomp.) |
| —$(CH_2)_3$— | | $CH_3$ | $2HCl.2H_2O$ | 255 | (Decomp.) |
| —$(CH_2)_3$— | | $C_2H_5$ | — | 273–5 | (Decomp.) |
| —$(CH_2)_3$— | | $C_2H_5$ | 2HCl | 290 | (Decomp.) |
| —$(CH_2)_4$— | | $CH_3$ | — | 63–5 | (Decomp.) |
| —$(CH_2)_4$— | | $CH_3$ | $2HCl.2H_2O$ | 250–2 | (Decomp.) |

Bisamidine derivatives of substituted phenanthridines of the formula Ic which are preferred in accordance with the invention are those in which R denotes hydrogen, the amidino groups are in the 3-position and 8-position, $R_1$ represents hydrogen or an alkyl group, $R_2$ and $R_3$ each individually denote a $C_1$-$C_6$-alkyl group or, together with the nitrogen atom to which they are attached, form a heterocyclic group, $R_1$ and $R_2$, together with the carbon atom and the nitrogen atom to which they are attached, form a heterocyclic structure, and Z represents hydrogen, halogen, $C_1$-$C_6$-alkoxy, amino, $C_1$-$C_6$-alkylamino, di-$C_1$-$C_6$-alkylamino or an appropriate heterocyclic group, and also pharmaceutically acceptable salts thereof.

Some new bisamidine derivatives of 6-substituted phenanthridines are listed in the following table:

| $R_1$ | $R_2$ | $R_3$ | Z | Salt | Mp. (°C.) |
|---|---|---|---|---|---|
| H | $CH_3$ | $CH_3$ | $N(C_2H_5)_2$ | — | 130-2 |
| H | $CH_3$ | $CH_3$ | $N(C_3H_7-n)_2$ | — | Oil |
| H | $C_2H_5$ | $C_2H_5$ | $N(CH_3)_2$ | — | 124-26 |
| H | $C_2H_5$ | $C_2H_5$ | $N(C_2H_5)_2$ | — | 126-7 |
| H | $C_2H_5$ | $C_2H_5$ | $N(C_3H_7-n)_2$ | — | Oil |
| $CH_3$ | $CH_3$ | $CH_3$ | $N(CH_3)_2$ | — | 144-46 |
| $CH_3$ | $CH_3$ | $CH_3$ | $N(C_2H_5)_2$ | — | 130-2 |
| $CH_3$ | $CH_3$ | $CH_3$ | $N(C_3H_7-n)_2$ | — | 139 |
| $CH_3$ | $CH_3$ | $CH_3$ | $N(C_3H_7-n)_2$ | $3HCl.2H_2O$ | — |
| $CH_3$ | $C_2H_5$ | $C_2H_5$ | $N(CH_3)_2$ | — | 118-21 |
| $CH_3$ | $C_2H_5$ | $C_2H_5$ | $N(C_2H_5)_2$ | — | 132-33 |
| $CH_3$ | $C_2H_5$ | $C_2H_5$ | $N(C_2H_5)_2$ | $3HCl.3H_2O$ | 220-2 (Decomp.) |
| $CH_3$ | $C_2H_5$ | $C_2H_5$ | $N(C_3H_7-n)_2$ | — | 146-47 |
| $CH_3$ | $C_2H_5$ | $C_2H_5$ | pyrrolidine | — | 152-54 |
| $CH_3$ | $C_2H_5$ | $C_2H_5$ | 4-methylpiperidine | — | 151-53 |
| $CH_3$ | $C_2H_5$ | $C_2H_5$ | 4-methylpiperazine | — | 160-61 |
| $CH_3$ | $C_2H_5$ | $C_2H_5$ | morpholine | — | 179-81 |
| $CH_3$ | $C_2H_5$ | $C_2H_5$ | 4-phenylpiperidine | — | 155-56 |
| $C_2H_5$ | $CH_3$ | $CH_3$ | $N(CH_3)_2$ | — | 160-62 |
| $C_2H_5$ | $CH_3$ | $CH_3$ | $N(C_2H_5)_2$ | — | 104-6 |
| $C_2H_5$ | $CH_3$ | $CH_3$ | $N(C_3H_7-n)_2$ | — | 111-13 |
| H | $-(CH_2)_4-$ | | $N(CH_3)_2$ | — | 202-3 |
| H | $-(CH_2)_4-$ | | $N(C_2H_5)_2$ | — | 149-50 |
| H | $-(CH_2)_4-$ | | $N(C_3H_7-n)_2$ | — | 183-86 |
| H | $-(CH_2)_5-$ | | $N(CH_3)_2$ | — | 164-65 |
| H | $-(CH_2)_5-$ | | $N(C_3H_7-n)_2$ | — | 134-36 |
| $-(CH_2)_3-$ | | H | $N(C_3H_7-n)_2$ | — | 167-70 |
| $-(CH_2)_3-$ | | $CH_3$ | $N(CH_3)_2$ | — | 181-82 |
| $-(CH_2)_3-$ | | $CH_3$ | $N(C_2H_5)_2$ | — | 144-45 |
| $-(CH_2)_3-$ | | $CH_3$ | $N(C_3H_7-n)_2$ | — | 152-53 |
| $-(CH_2)_3-$ | | $CH_3$ | pyrrolidine | — | 110-12 |
| $-(CH_2)_3-$ | | $CH_3$ | morpholine | — | 112-14 |
| $-(CH_2)_4-$ | | $CH_3$ | $N(C_2H_5)_2-$ | — | 135-37 |
| $-(CH_2)_4-$ | | $CH_3$ | $N(C_3H_7-n)_2$ | — | 141-42 |
| $-(CH_2)_4-$ | | $CH_3$ | pyrrolidine | — | 124-25 |
| $-(CH_2)_4-$ | | $CH_3$ | morpholine | — | 124-25 |

The present invention also relates to a process for the preparation of the new bisamidine derivatives of polycyclic molecules of the formula I.

The bisamidine derivtives of the 5,10-dioxo-4,5,9,10-tetrahydro-4,9-dioxapyrene of the formula Ia and pharmaceutically acceptable salts thereof are prepared by reacting a compound of the formula II

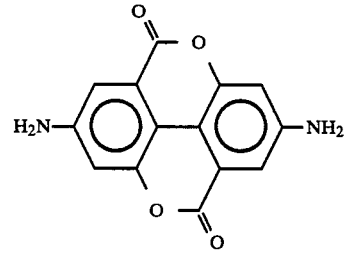

with an inorganic acid halide, such as, for example, phosphorus oxychloride, and an amide of the formula

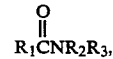

in which $R_1$, $R_2$ and $R_3$ have the meanings mentioned above, and, if desired, converting the resulting compound of the formula Ia into the said salts in a known manner.

The starting compound of the formula II is obtained in accordance with the process described by Migachev., G. I. (Zh. Vses. Khim. Obstich. 24 (1979), 3, 307-309).

The reaction of the compound of the formula II with an inorganic acid halide and an amide of the formula

can be accelerated or completed by heating the reaction mixture at 50°–80° C., preferably at 60° C.

If appropriate, the reaction can be carried out in solvents, such as halogenated hydrocarbons, for example chloroform or methylene chloride, or in ethers, such as dioxane or tetrahydrofuran.

Bisamidine derivatives of the 6(5H)-phenanthridone of the formula Ib are obtained by reacting the 3,8-diamino-6(5H)-phenanthridone (III)

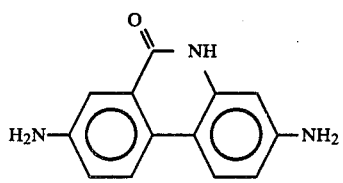

which can be obtained by the process described by M. Devis (J. Chem. Soc. (1956), 337), with phosphorus oxychloride and an appropriately substituted amide of the formula

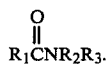

The reaction can be accelerated or completed by heating the reaction mixture at 50° C. If desired, the reaction can be carried out in solvents, such as halogenated hydrocarbons, for example chloroform or methylene chloride, or in ethers, such as, for example, dioxane or tetrahydrofuran.

Bisamidine derivatives of phenanthridines of the formula Ic are obtained by reacting a compound of the formula IV

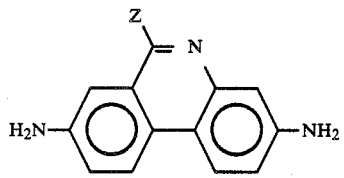

in which R and Z have the meaning mentioned above, with an inorganic halide, such as phosphorus oxychloride, and an amide of the formula

in which $R_1$, $R_2$ and $R_3$ have the meanings mentioned above. The corresponding pharmaceutically acceptable salts are obtained by converting the resulting compound of the formula Ic into the said salts in a customary manner.

The starting compounds of the formula VI in which R has the meaning mentioned above and Z represents $C_1$–$C_6$-alkylamino, di-$C_1$–$C_6$-alkylamino or a nitrogen-containing heterocyclic group optionally containing a second nitrogen, oxygen or sulfur atom are obtained by reacting 6-chloro-3,8-dinitrophenanthridine (Albert A. I., Chem. Soc., 1284, 1948) with corresponding amines in a known manner (Keene, S. R. T., Turner, G. L., Tetrahedron 27 (15), 3405, 1971) and subsequently reducing the compound obtained thereby with hydrazine hydrate/alcohol in the presence of a palladium-on-charcoal catalyst (Flechter, T. L.; J. Med. Chem., 12, 822, 1969).

The reaction of the compound of the formula IV with phosphorus oxychloride and an amide of the formula

can be accelerated or completed by heating the reaction mixture at 60°–90° C., preferably 80° C., and can, if desired, also be carried out in solvents, such as halogenated hydrocarbons, for example chloroform or methylene chloride, or in ethers, such as dioxane or tetrahydrofuran.

The compound of the formula Ic can also be prepared by reacting compounds of the formula Ib with an inorganic halide, such as phosphorus oxychloride, a 6-chloro derivative of the formula V

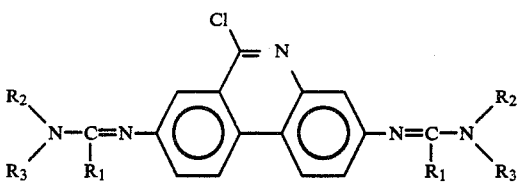

being obtained, and subsequently reacting the resulting compound with an appropriate amine.

The substituted bisamidine derivatives, according to the invention, of the 5,10-dioxo-4,5,9,10-tetrahydro-4,9-dioxapyrene, of the 6(5H)-phenanthridone and of the 6-substituted phenanthridine are distinguished by an antiprotozoal activity.

The in vitro activity of the compounds was tested in a monophase medium on a polyaxenic culture of Entamoeba histolytica. The compounds are effective within a concentration range of 50–200 mcg/ml.

The in vivo activity of the compounds was tested by the method of Jarumilinta (Ann. Trop. Med. Paras. 66, 2, 139–145, 1966) on golden hamsters which had been infected with hepatitis viruses. The compounds were effective at dosages from 4×30 mg/kg up to 4×200 mg/kg. The in vivo activity against infections of the cecum in Wistar rats was tested by a modification of Jones's method (Ann. Trop. Med. Paras. 40, 130–140, 1946). The compounds proved effective at dosages of 4×225–300 mg/kg.

The activity of the compounds against trichomonads was tested in vitro using Trichomonas vaginalis on a modified CPLM culture medium (Chatterjee and Ray, J. Parasit., 65 (5) 815–816, 1979). The compounds proved effective at doses of 100–200 mcg/ml.

The following examples illustrate the present invention.

EXAMPLE 1

2,7-Di-(N',N'-dimethylaminomethyleneamino)-5,10-dioxo-4,5-9,10-tetrahydro-4,9-dioxapyrene hydrochloride A suspension of 2,7-diamino-5,10-dioxo-4,5,9,10-tetrahydro-4,9-dioxapyrene (300 mg) in N,N-diethylformamide (6 ml) was added to a mixture of phosphorus oxychloride (1.8 ml) and N,N-diethylformamide (4 ml), the temperature of the mixture being kept at 5° C. The resulting mixture was stirred for 30 minutes at room temperature, heated at 60° C. for 5 hours, cooled, and diluted with acetone. The resulting precipitate was filtered off and dissolved in water. The pH of the clear solution was adjusted to a value of 9 with aqueous ammonia, and the resulting precipitate was filtered off, washed with water, dried, and purified by column chromatography over an aluminum oxide column, using benzene as the mobile phase.

The solid thus obtained was converted into its hydrochloride by reaction with an ethereal solution of hydrochloric acid. The hydrochloride crystallized out from an ethanol/ether mixture. Yield 55%, melting point 282° C. (decomposition).

EXAMPLE 2

2,7-Di-(N',N'-diethylaminoethylideneamino)-5,10-dioxo-4,5,9,10-tetrahydro-4,9-dioxapyrene As in Example 1, but using N,N-diethylacetamide instead of N,N-diethylformamide and without converting the resulting compound into its hydrochloride. Yield 69%, melting point 220°–222° C. (CHCl$_3$/methanol).

EXAMPLE 3

2,7-Di-(N',N'-diethylaminoethylidineamino)-5,10-dioxo-4,5,9,10-tetrahydro-4,9-dioxapyrene hydrochloride The 2,7-di-(N',N'-diethylaminoethylideneamino)-5,10-dioxo-4,5,9,10-tetrahydrodioxapyrene obtained in Example 2 was converted into its hydrochloride by the process described in Example 1, paragraph 2. Yield 88%, melting point 284°–286° C. (decomposition) (ethanol/ether).

EXAMPLE 4

2,7-Di-(N-methylpyrrolidin-2-ylideneamino)-5,10-dioxo-4,5,9,10-tetrahydro-4,9-dioxapyrene hydrochloride As in Example 1, but using N-methyl-2-pyrrolidone instead of N,N-diethylformamide. Yield 58%, melting point 300° C. (decomposition) (ethanol/ether).

EXAMPLE 5

2,7-Di-(N-methylpiperid-2-ylideneamino)-5,10-dioxo-4,5,9,10-tetrahydro-4,9-dioxapyrene hydrochloride As in Example 1, but using N-methyl-2-piperidone instead of N,N-diethylformamide. Yield 62%, melting point 277°–279° C. (decomposition) (ethanol/ether).

EXAMPLE 6

2,7-Di-(piperidinomethyleneamino)-5,10-dioxo-4,5,9,10-tetrahydro-4,9-dioxapyrene hydrochloride monohydrate As in Example 1, but using N-formylpiperidine instead of N,N-diethylformamide. Yield 59%, melting point 290°–293° C. (decomposition) (ethanol/ether).

EXAMPLE 7

2,7-Di-(pyrrolidinomethyleneamino)-5,10-dioxo-4,5,9,10-tetrahydro-4,9-dioxapyrene A suspension of 2,7-diamino-5,10-dioxo-4,5,9,10-tetrahydro-4,9-dioxapyrene (500 mg) in tetrahyrofuran (4 ml) was added to a mixture of phosphorus oxychloride (0.7 ml) and N-formylpyrrolidine (2 ml) and tetrahydrofuran (4 ml), the temperature of the mixture being kept at 5° C. The resulting mixture was stirred for 30 minutes at room temperature, heated at 80° C. for 1 hour and worked up as described in Example 1, paragraph 1. Yield 68%, melting point 275° C. (decomposition) (CHCl$_3$/methanol).

EXAMPLE 8

3,8-Di-(N',N'-dimethylaminoethylideneamino)-6(5H)-phenanthridone dihydrochloride dihydrate A suspension of 3,8-diamino-6(5H)-phenanthridone (500 mg) in N,N-dimethylacetamide (1.5 ml) was added to a mixture of phosphorus oxychloride (1.5 ml) and N,N-dimethylacetamide (5 ml), the temperature of the mixture being kept at 5° C. The resulting mixture was stirred for 30 minutes at room temperature, heated at 45°–50° C. for 1 hour, cooled, and diluted with acetone. The precipitate obtained thereby was filtered off and dissolved in water. The pH of the clear solution was adjusted to a value of 9–10 with aqueous ammonia. The solid thus formed was filtered off, washed with water, dried, and purified by column chromatography over an aluminum oxide column using benzene and chloroform as the mobile phase. The solid obtained was converted into its hydrochloride and the latter was recrystallized from methanol/ether. Yield 85%, melting point 268°–270° C. (decomposition).

EXAMPLE 9

3,8-Di-(N',N'-dimethylaminomethyleneamino)-6(5H)-phenanthridone

As in Example 8, but using N,N-diethylformamide instead of N,N-dimethylacetamide and without converting the resulting compound into the hydrochloride. The product crystallized out from chloroform/methanol. Yield 75%, melting point 240°–241° C. (decomposition).

EXAMPLE 10

The compound obtained in Example 9 was converted into its hydrochloride by the process described in Example 1, paragraph 2. Yield 90%, melting point 281°–283° C. (decomposition) (ethanol/ether).

EXAMPLE 11

3,8-Di-(N-methylpyrrolidin-2-ylideneamino)-6(5H)-phenanthridone dihydrochloride dihydrate As in Example 8, but using N-methyl-2-pyrrolidone instead of N,N-dimethylacetamide. Yield 72%, melting point 255° C. (decomposition).

EXAMPLE 12

3,8-Di-(piperidinomethyleneamino)-6(5H)-phenanthridone dihydrochloride

As in Example 8, but using N-formylpiperidine instead of N,N-dimethylacetamide. Yield 86%, melting point 255°–257° C. (decomposition).

EXAMPLE 13

3,8-Di-(pyrrolidinomethyleneamino)-6(5H)-phenanthridone

A suspension of 3,8-diamino-6-(5H)-phenanthridone (500 mg) in tetrahydrofuran (5 ml) was added to a mixture of phosphorus oxychloride (0.75 ml) and N-formylpyrrolidine (2.5 ml) and tetrahydrofuran (5 ml), the temperature of the mixture being kept at 5° C. The resulting mixture was stirred for 30 minutes at room temperature, heated at 50° C. for 1 hour and worked as described in Example 8, paragraph 1. Yield 52%, melting point 280° C. (decomposition) ($CHCl_3$/methanol).

EXAMPLE 14

3,8-Di-(N-diethylaminomethyleneamino)-6-dimethylaminophenanthridine

A suspension of 3,8-diamino-6-dimethylaminophenanthridine (500 mg) in N,N-diethylformamide (2 ml) was added to a mixture of phosphorus oxychloride (1.5 ml) and N,N-diethylformamide (5 ml), the temperature of the mixture being kept at 5° C. The resulting mixture was stirred for 30 minutes at room temperature, heated at 75°–80° C. for 2 hours, cooled, and diluted with acetone. The precipitate formed was filtered off and dissolved in water. The pH of the clear solution was adjusted to a value of 9 with aqueous ammonia. The solid thus obtained was filtered off, washed with water, dried, and purified by column chromatography over a neutral aluminum oxide column using benzene as the mobile phase. The product crystallized out from chloroform/diisopropyl ether. Yield 71%, melting point 124°–126° C.

EXAMPLE 15

6-Diethylamino-3,8-di-(pyrrolidinomethyleneamino)-phenanthridine

As in Example 14, but using 3,8-diamino-6-diethylaminophenanthridine and N-formylpyrrolidine instead of 3,8-diamino-6-dimethylaminophenanthridine and N,N-diethylformamide. Yield 66%, melting point 149°–150° C. (chloroform/petroleum ether (60°–80° C.)).

EXAMPLE 16

3,8-Di-(N,N-dimethylaminoethylideneamino)-6-dipropylaminophenanthridine

As in Example 14, but using 3,8-diamino-6-dipropylaminophenanthridine and N,N-dimethylacetamide instead of 3,8-diamino-6-dimethylaminophenanthridine and N,N-diethylformamide. Yield 60%, melting point 139° C. (chloroform/diisopropyl ether).

EXAMPLE 17

3,8-Di-(N,N-dimethylaminoethylideneamino)-6-dipropylaminophenanthridine trihydrochloride The 3,8-di-(N,N-dimethylaminoethylideneamino)-6-dipropylaminophenanthridine obtained in Example 16 was converted into its hydrochloride by treatment in methanol with an ethereal solution of hydrochloric acid. Yield 95%.

EXAMPLE 18

3,8-Di-(N-methylpyrrolidin-2-ylideneamino)-6-morpholinophenanthridine

As in Example 14, but using 3,8-diamino-6-morpholinophenanthridine and N-methyl-2-pyrrolidone instead of 3,8-diamino-6-dimethylaminophenanthridine and N,N-diethylformamide. Yield 35%, melting point 112°–114° C. (petroleum ether 60°–80° C.)).

EXAMPLE 19

3,8-Di-(N,N-diethylaminoethylideneamino)-6-(N'-methylpiperazino)-phenanthridine

As in Example 14, but using 3,8-diamino-6-(N-methylpiperazino)-phenanthridine and N,N-diethylacetamide instead of 3,8-diamino-6-dimethylaminophenanthridine and N,N-dimethylformamide. Yield 78%, melting point 160°–161° C. (diisopropyl ether/petroleum ether (60°–80° C.)).

EXAMPLE 20

3,8-Di-(N,N-diethylaminoethylideneamino)-6-(4-phenylpiperidino)-phenanthridine

As in Example 14, but using 3,8-diamino-6-(4-phenylpiperidino)-phenanthridine and N,N-diethylacetamide instead 3,8-diamino-6-dimethylaminophenanthridine and N,N-diethylformamide. Yield 75%, melting point 155°–156° C. (diisopropyl ether).

EXAMPLE 21

3,8-Di-(N-methylpyrrolidin-2-ylideneamino)-6-dipropylaminophenanthridine

A suspension of 3,8-diamino-6-dipropylaminophenanthridine (500 mg) in tetrahydrofuran (4 ml) was added to a mixture of phosphorus oxychloride (1.5 ml) and N-methyl-2-pyrrolidone (5 ml) and tetrahydrofuran (4 ml), the temperature of the mixture being kept at 5° C. The resulting mixture was stirred for 30 minutes at room temperature, heated at 80° C. for 3 hours and worked up as described in Example 14. Yield 62%, melting point 152°–153° C. (diisopropyl ether/petroleum ether (60°–80° C.)).

EXAMPLE 22

3,8-Di-(N-methylpiperidin-2-ylideneamino)-6-pyrrolidinophenanthridine

As in Example 21, but using 3,8-diamino-6-pyrrolidinophenanthridine instead of 3,8-diamino-6-dipropylaminophenanthridine and using dioxane instead of tetrahydrofuran. Yield 28%, melting point 124°–125° C. (chloroform/petroleum ether (60°–80° C.)).

We claim:

1. A compound of the formula I in which
- R denotes hydrogen, $C_1$–$C_3$-alkyl, $C_1$–$C_3$-alkoxy, halogen, nitro or amino,
- $R_1$ denotes hydrogen, a $C_1$–$C_6$-alkyl group which is unsubstituted or substituted by the amino or di-$C_1$–$C_3$-alkylamino group, or a di-$C_1$–$C_3$-alkylamino group,
- $R_2$ and $R_3$ individually denote a $C_1$–$C_6$-alkyl group or, together with the nitrogen atom to which they are attached, denote pyrrolidine, piperidine, imidazoline or pyrimidine, or $R_1$ and $R_2$, together with the carbon atom and the nitrogen atom to which they are attached, denote pyrrolidine or piperidine,
- X and Z each denote oxygen or
- X represents the —NH— group and Z represents oxygen or
- X represents nitrogen and Z represents hydrogen, halogen, $C_1$–$C_6$-alkoxy, amino, mono-$C_1$–$C_6$-alkylamino, di-$C_1$–$C_6$-alkylamino, N-alkyl substituted piperazine, piperidine, morpholine, pyrrolidine, or alkyl or phenyl substituted piperidine, and
- Y represents hydrogen or, if X and Z each denote oxygen, represents the bridge $$-O-\underset{\underset{O}{\|}}{C}-,$$

which forms an additional ring system,
and pharmaceutically acceptable salts thereof.

2. A compound as claimed in claim 1, of the formula Ia in which R, $R_1$, $R_2$ and $R_3$ have the meanings indicated in claim 1.

3. A compound as claimed in claim 1 of the formula Ib in which R, $R_1$, $R_2$ and $R_3$ have the meanings indicated in claim 1.

4. A compound as claimed in claim 1 of the formula Ic in which R, $R_1$, $R_2$, $R_3$ and Z have the meanings indicated in claim 1.

5. A pharmaceutical product for combating protozoal infections which contains an effective amount of a compound of the formula I as claimed in claim 1 as the active compound, in a mixture or combination with a pharmaceutically acceptable excipient and/or stabilizer.

6. The use of a compound of the formula I as claimed in claim 1 for combating protozoal infections.

* * * * *